(12) United States Patent
Mehra et al.

(10) Patent No.: US 6,817,256 B2
(45) Date of Patent: Nov. 16, 2004

(54) PIPETTE SAMPLING SYSTEM

(75) Inventors: Ravinder C. Mehra, Princeton, NJ (US); Zygmunt M. Andrevski, Princeton, NJ (US); Zvi G. Loewy, Fair Lawn, NJ (US)

(73) Assignee: Alfa Wassermann, Inc., West Caldwell, NJ (US)

( * ) Notice: Subject to any disclaimer, the term of this patent is extended or adjusted under 35 U.S.C. 154(b) by 0 days.

(21) Appl. No.: 10/085,687

(22) Filed: Feb. 26, 2002

(65) Prior Publication Data

US 2002/0134175 A1 Sep. 26, 2002

Related U.S. Application Data

(60) Provisional application No. 60/271,829, filed on Feb. 27, 2001.

(51) Int. Cl.[7] .................................................. G01N 1/00
(52) U.S. Cl. .................................................. 73/863.85
(58) Field of Search ........................ 73/863.81, 863.85, 73/864.01, 864.22; 422/100, 101

(56) References Cited

U.S. PATENT DOCUMENTS

| | | | | |
|---|---|---|---|---|
| 4,492,634 A | * | 1/1985 | Villa-Real | 210/398 |
| 4,973,450 A | * | 11/1990 | Schluter | 422/101 |
| 5,147,613 A | * | 9/1992 | Heilmann et al. | 422/116 |
| 5,263,934 A | * | 11/1993 | Haak | 604/110 |
| 5,483,843 A | * | 1/1996 | Miller et al. | 73/864.23 |
| 5,517,867 A | * | 5/1996 | Ely et al. | 73/863.85 |
| 5,919,356 A | * | 7/1999 | Hood | 210/85 |
| 6,117,394 A | * | 9/2000 | Smith | 422/100 |
| 6,180,060 B1 | * | 1/2001 | Green et al. | 422/64 |
| 6,274,087 B1 | * | 8/2001 | Preston et al. | 422/100 |

* cited by examiner

Primary Examiner—Charles D Garber
(74) Attorney, Agent, or Firm—Frommer Lawrence & Haug LLP

(57) ABSTRACT

The invention relates to a pipette sampling system that allows for automated sampling from the contents of a capped sample tube. More specifically, the invention relates to a pipette tip, having a piercing tip attached thereto, for removal of aliquots of samples from capped sample tubes comprising said samples.

7 Claims, 6 Drawing Sheets

PIPETTE SAMPLING SYSTEM

CROSS-REFERENCE TO RELATED APPLICATIONS

This application claims benefit of and priority to U.S. application Ser. No. 60/271,829, filed Feb. 27, 2001, herein incorporated by reference.

FIELD OF THE INVENTION

The invention relates to a pipette sampling system that allows for the removal of biological samples from capped containers. More specifically, the invention relates to a pipette tip having a piercing tip attached thereto.

BACKGROUND OF THE INVENTION

The elucidation of the complete genome sequences of a multitude of prokaryotic and eukaryotic organisms, including in particular, humans, has created the foundation for comprehensive genome analysis. Microarray gene-expression analysis, DNA diagnostics, and gene-based drug discovery, among other applications, rely on knowledge of and access to the genome sequence. The human genome contains approximately three billion base pairs contained within 24 separate chromosomes harboring an estimated total of 30,000 distinct genes, each of which has an average protein-encoding length of about 3,000 base pairs. Further, it has been established that the genetic content comprising the totality of genes identified in the human genome accounts for only about ten percent of the total nucleotide sequence. The function of the remaining portion of the genome is not yet fully understood.

Concomitant with the recent completion of the sequencing of the human genome, a large-scale global effort has evolved, which includes scientists from academic, private, and government research institutions, to understand the functions of all of the novel genes identified, the protein products they encode, and the complex interactions of these components. It is widely believed that this research will have an immediate and profound effect on future understanding of biochemical, genetic, and physiological processes, as well as on the diagnosis and treatment of medical conditions.

In particular, the technology of genotyping is developing at a rapid pace. This technology links various human disease and molecular traits to specific variations found in genes. These variations are defined in terms of a specific section of a gene that, when the sequence of nucleotides in that section changes, a corresponding defect in the protein or other material synthesized from the gene occurs. These portions of the gene are called single-nucleotide polymorphisms, or SNPs. SNPs can be used to predict if an individual is likely to develop a certain disease or if certain drugs will be effective when administered to the individual. This technology is of immense interest to pharmaceutical companies since the SNPs that control responses to a drug can be used to develop tests for the screening of patients prior to the prescription of a drug, which in turn could prove beneficial for the lowering of adverse drug reactions through the identification of susceptible individuals. Further, drug research will be made more efficient since knowledge of SNPs will help define new drugs and will help determine and document the therapeutic effectiveness of a given pharmaceutical compound.

Disclosure of the human genome sequence has created, virtually overnight, a plethora of methods for studying DNA, RNA, and other biological macromolecules such as protein. New whole-genome sequences from a wide variety of organisms are currently being generated at an increasingly high rate. Sequences and the expression patterns of genes are compared and contrasted for differences or similarities in an effort to further the understanding of human biology at genetic, biochemical, and physiological levels. The rapid generation, examination, analysis, and comparative analysis of whole-genome nucleic acid sequences from biological organisms in the art has been termed "genomics".

The field of genomics can be divided into two major areas: (a) functional genomics, which attempts to interpret the functions of genes, including the investigation of gene expression and gene control and (b) comparative genomics, which studies the human genome through comparisons to the genomes of non-humans to gain insight into gene function and the evolution of genes, proteins, and organisms. Further, the related discipline of bioinformatics has developed concomitant with the expansion of genomics. This rapidly evolving field has been defined as one that integrates computational approaches for the manipulation and interpretation of the massive amount of nucleotide and protein sequence information currently being generated in the art. The development of new computers, software, and methods of data mining are critical components of this technology.

Although there are a multitude of steps comprising genomic analysis, it is often the case that the initial stages of genomics methodologies are the rate-limiting steps of the complete process. Nucleic acid purification is an example of one such process occurring in the initial stages of genomics methods that can affect the overall speed of the process. In the current art, the purification of nucleic acids is still largely carried out in small batches by trained technicians. Moreover, the technician is limited to processing a small number of samples per day and to producing lower yields of nucleic acids. This limits the ability to generate nucleotide sequence information, exposes the technician to infective agents, risks contamination of the samples, and wastes resources. Therefore, the purification of nucleic acids can represent an important rate-determining step of genomics methodologies.

One technique to increase the efficiency, productivity, and quality of biological macromolecule purification would be to employ automated methods. Several semi-automated methods of sample processing are available for the purification of nucleic acids, but still require human intervention and are not high-throughput. For example, U.S. Pat. No. 5,270,211 relates to a sample tube entry port for an automatic chemical analyzer that facilitates removal of samples by the pipette without exposing the operator to accidental contact with liquid materials in the draw tube.

Fully-automated systems are also available for the purification of nucleic acids but are not widely used due to their inflexibility and high cost. These systems are typically used in dedicated high-volume applications such as those found in large genetics testing laboratories that focus on the isolation and purification of DNA from particular types of samples. Fully-automated systems are generally not used in smaller laboratories where there typically exists a greater diversity of biological sample types from which nucleic acids are purified on a regular basis. Currently, fully-automated systems also suffer from the lack of flexibility in sample volume and typically are designed for small-volume samples. Further, the integrity, purity, concentration, and yield of the nucleic acids tends to be low.

Another initial stage in genomics methodologies is the sampling of biological samples. This step is sometimes referred to as 'front-end' in that it occurs early in the process and further, it can determine the rate of the whole process, particularly when large numbers of tubes must be sampled. Sampling a biological sample, such as blood, is typically performed by aspirating a defined volume of fluid from a container, typically an uncapped test tube. Racks of uncapped sample tubes are common to many clinical laboratories.

Since biological samples are frequently the source of hazardous materials (bacteria, viruses, fungi, biological toxins), they can pose dangers to laboratory technicians and health care workers in many different work settings, including clinical and research laboratories. Further, handling of samples by technicians can often lead to the inadvertent contamination of the biological samples from microorganisms contained on and in the environment around the technician. In other words, the technician must maintain caution and careful handling measures so as not to be contaminated from, or cause contamination to, the sample.

Once the caps are removed from the tubes, the samples are no longer sealed and contamination moving into the tube or contamination being released from the tube can occur inadvertently, even when using the most carefully observed measures. It would be preferable if sampling could occur directly from sealed tube in a manner such that the caps would not have to be removed during the process. Subsequent to sample obtainment, the defined volumes of biological samples are then individually processed through a variety of steps to yield purified biological macromolecules, such as nucleic acids.

In view of the problems in the art mentioned heretofore, there exists a need for a pipette sampling system that allows for the removal of biological samples from sample tubes in a safe, closed-tube, and "hands-free" manner. There is a further need for a closed-tube pipette sampling system that is automated or semi-automated, and which can be integrated with downstream automated and non-automated processing systems for biological macromolecule purification, including but not limited to the purification of nucleic acid and protein. There exists a still further need for a closed-tube pipette sampling system that can accommodate a flexible range of sample volumes and biological sample types including, but not limited to, whole blood, plasma, spinal fluid, serum, saliva, sputum, urine, feces, Buccal cells, spermatozoa, solid tissue, bacteria, yeast, viral samples, semen, cultured cell lines, plants and combinations thereof. A still further need exists for a pipette sampling system that eliminates or minimizes the potential for sample or operator contamination, is able to sample from a plurality of tubes, and has a low cost.

SUMMARY AND OBJECTS OF THE INVENTION

In accordance with one embodiment of the present invention, a device is provided for removing an aliquot of a biological sample from a closed receptacle comprising said biological sample, comprising a hollow chamber of predefined volume having inner and outer walls and top and bottom ends, a hollow piercing tip having sharp and blunt ends, wherein the blunt end is engaged to the bottom end of the hollow chamber, and a filter barrier engaged to the inner walls of the hollow chamber for preventing cross-contamination of fluids, aerosols, or samples beyond said chamber of predefined volume.

In accordance with another embodiment of the present invention, a method is provided for removing an aliquot of a biological sample from a closed receptacle comprising said biological sample, comprising piercing said closed receptacle with a device comprising a hollow chamber of predefined volume having inner and outer walls and top and bottom ends, a hollow piercing tip having sharp and blunt ends, wherein the blunt end is engaged to the bottom end of the hollow chamber, and filter means engaged to the inner walls of the hollow chamber for preventing cross-contamination of fluids, aerosols, or samples beyond said chamber of predefined volume, and aspirating a predefined volume of said biological sample into said hollow chamber.

In accordance with yet another embodiment of the present invention, a sampling tube system is provided for removing an aliquot of a biological sample from a sealed sample tube comprising said biological sample, comprising a loading arm comprising at least one inflatable membrane holder for reversibly engaging said sample tube for aspiration of the biological sample from the sample tube, a transfer arm comprising a positioning element reversibly engaged to the loading arm for rotating the loading arm and inverting said sample tube, a pipette tip reversibly engaged to the transfer arm comprising a filter barrier, a chamber of predefined volume and a piercing tip for piercing said sample tube, an aspiration tube affixed onto said pipette tip for aspirating said biological sample once the piercing tip has pierced said sample tube, and, optionally, a pipette strip holder for holding said pipette tips.

In accordance with still another embodiment of the present invention, a device is provided for removing an aliquot of biological sample from a sealed receptacle comprising said biological sample, comprising a hollow chamber of predefined volume having inner and outer walls and top and bottom ends, a hollow piercing tip having sharp and blunt ends, wherein the blunt end is engaged to the bottom end of the hollow chamber, a filter barrier engaged to the inner walls of the hollow chamber, a side vent positioned within the hollow chamber and between the filter barrier and piercing tip and a deflector plate separating the hollow chamber and the side vent, wherein the deflector substantially prevents or blocks excess sample from entering into the side vent.

In accordance with a still further embodiment of the present invention, a device is provided for removing an aliquot of biological sample from a sealed receptacle comprising said biological sample, comprising a hollow chamber of predefined volume having inner and outer walls and top and bottom ends, a hollow piercing tip having sharp and blunt ends, wherein the blunt end is engaged to the bottom end of the hollow chamber, a filter barrier engaged to the inner walls of the hollow chamber, and a side vent positioned within the hollow chamber and between the filter barrier and piercing tip, wherein the blunt end of the piercing tip substantially prevents or blocks excess sample from entering into the side vent.

In accordance with yet a still further embodiment of the present invention a device is provided for removing an aliquot of a sample from a sealed receptacle comprising said sample, comprising a hollow chamber of predefined volume having inner and outer walls and top and bottom ends, a hollow piercing tip having sharp and blunt ends, wherein the blunt end is engaged to the bottom end of the hollow chamber, and a filter barrier engaged to the inner walls of the hollow chamber.

In accordance with another embodiment of the present invention, a sampling tube system is provided for removing an aliquot of a sample from a sealed sample tube comprising said sample, comprising a loading arm comprising at least one inflatable membrane holder for reversibly engaging said sample tube for aspiration of the sample from the sample tube, a transfer arm comprising a positioning element reversibly engaged to the loading arm for rotating the loading arm and inverting said sample tube, a pipette tip reversibly engaged to the transfer arm comprising a filter barrier, a hollow chamber of predefined volume and a piercing tip for piercing said sample tube, an aspiration tube affixed onto said pipette tip for aspirating said sample once the piercing tip has pierced said sample tube, and optionally, a pipette strip holder for holding said pipette tips.

In accordance with a further embodiment of the present invention, a method is provided for sampling one or more samples from sealed sample tubes comprising said samples, comprising the steps of transferring said sample tube from a sample rack to a loading arm, wherein said sample tube is in an upright position, piercing said sample tube with a pipette tip comprising a piercing tip, inverting the pierced sample tube to a degree sufficient to maintain contact of the sample and the closure for a time sufficient to allow sample collection, aspirating said fluid from the pierced sample tube into a chamber within the pipette tip, reinverting the pierced tube to the upright position, and withdrawing the piercing tip from the sample tube.

In accordance with still another embodiment of the present invention, a device is provided for removing an aliquot of a sample from a sealed receptacle comprising said sample, comprising a hollow chamber of predefined volume having inner and outer walls and top and bottom ends, a hollow piercing tip having sharp and blunt ends, wherein the blunt end is engaged to the bottom end of the hollow chamber, a filter barrier engaged to the inner walls of the hollow chamber, a side vent positioned within the hollow chamber and between the filter barrier and piercing tip, and a deflector plate separating the hollow chamber and the side vent, wherein the deflector plate substantially prevents or blocks excess sample from entering into the side vent.

In accordance with still another embodiment of the present invention, a device is provided for removing an aliquot of sample from a sealed receptacle comprising said sample, comprising a hollow chamber of predefined volume having inner and outer walls and top and bottom ends, a hollow piercing tip having sharp and blunt ends, wherein the blunt end is engaged to the bottom end of the hollow chamber, a filter barrier engaged to the inner walls of the hollow chamber, and a side vent positioned within the hollow chamber and between the filter barrier and piercing tip, wherein the blunt end of the piercing tip substantially prevents or blocks excess sample from entering into the side vent.

In accordance with yet another embodiment of the present invention, a method is provided for preventing cross-contamination of an aliquot comprising a sample while removing said aliquot from a sealed receptacle comprising said sample, comprising the steps of piercing said sealed receptacle with a device comprising a hollow chamber of predefined volume having inner and outer walls and top and bottom ends; a hollow piercing tip having sharp and blunt ends, wherein the blunt end is engaged to the bottom end of the hollow chamber; and filter means engaged to the inner walls of the hollow chamber for preventing cross-contamination of fluids, aerosols, or samples beyond said hollow chamber, and aspirating a predefined volume of said sample into said hollow chamber.

One object of the current invention is to provide a pipette sampling system that allows for the removal of biological samples from sample tubes in a safe, closed-tube manner such that the risk of sample- or operator-contamination is eliminated. Another object of the current invention is to provide a closed-tube pipette sampling system, that is automated, semi-automated or manual, which can be integrated with downstream automated and non-automated processing systems for biological macromolecule purification, including but not limited to the purification of nucleic acid and protein. A further object of the current invention is to provide a closed-tube pipette sampling system that can accommodate a flexible range of sample volumes and biological sample types including, but not limited to, whole blood, plasma, spinal fluid, serum, saliva, sputum, urine, feces, Buccal cells, spermatozoa, solid tissue, bacteria, yeast, viral samples, semen, cultured cell lines, plants and combinations thereof. A still further objective of the current invention is to provide a closed-tube pipette sampling system that can sample from a plurality of tubes, employs disposable pipette tips and disposable piercing tips, has a low cost, and is suitable for a genomics platform.

The present invention encompasses methods and components for a pipette sampling system that provides closed-tube sampling of samples from sample tubes comprising a wide variety of sample types. Such sample types may be biological such as, for example, whole blood, plasma, spinal fluid, serum, saliva, sputum, urine, feces, Buccal cells, spermatozoa, solid tissue, bacteria, yeast, viral samples, semen, cultured cell lines, plants and combinations thereof. The sample types may also be chemical such as, for example, reagents, catalysts and the like. Indeed, a skilled artisan would readily understand that any sample type capable of being aspirated out of a sample tube may be utilized by the present invention.

The components comprising the current invention include, but are not limited to, a sample tube, preferably but not limited to a Vacutainer™ (Becton Dickinson), a pipette tip, preferably a disposable pipette tip, and a sampling tube system, preferably requiring no human intervention. Further, the invention can be automated or semi-automated, can provide sampling from a plurality of sample tubes, and can be integrated with downstream automated and non-automated processing systems for biological macromolecule purification, including but not limited to, the purification of nucleic acid and protein.

In one embodiment, the pipette tip comprises a main chamber of defined volume, a filter barrier, and a piercing tip. Preferably, the piercing tip is designed to penetrate a closure of the sample tube without the destruction or removal of the tube closure. The piercing tip can be made of any non-reactive material known in the art, including, for is example, stainless steel, plastics, polypropylene and polystyrene.

The sample tube is comprised of a hollow chamber with an orifice at the top end and a closed surface at the bottom end. It is preferable that the sample tube is a vacuum collection tube such as that embodied by, but not limited to, a Vacutainer™ (manufactured by Becton Dickenson). Preferably, the filter barrier of the pipette tip is sufficient to prevent cross-contamination of samples, fluids, or aerosols and/or fluid uptake or movement beyond the chamber, such as into instrument lines or components. More preferably, the filter barrier is a hydrophobic sterilizable filter barrier, such as, for example, Porex.™ Preferably, the pipette tip and the piercing tip are designed and adapted to pierce the closure of the sample tube, are disposable, and come pre-sterilized.

The pipette tip allows aspiration of aliquot samples from sample tubes. Such aliquots can be from about 1 $\mu$l to about 5 ml in volume, preferably from about 5 µl to about 1 ml, or most preferably from about 20 µl to about 100 µl. Preferably, the pipette tip is designed and adapted for use in the closed-tube pipette sampling system and downstream automated and non-automated processing systems for biological macromolecule purification.

The present invention further comprises a sampling tube system that allows the pipette sampling system access to a sample contained in a tube so as to obtain a defined volume of the sample. The defined volume can be from about 1 µl to about 5 ml, or preferably from about 5 µl to about 1 ml, or most preferably from about 20 µl to about 100 µl. Further, it is preferable that the sample tube is sealed with a closure barrier that seals the tube and prevents the sample from leaking, spilling, or releasing aerosols. An example of a tube system available in the art that could be used is the Vacutainer™ tube, a type of vacuum collection tube (Becton Dickinson). These tubes are provided with ordinary rubber stoppers or with rubber stoppers covered by a plastic Hemogard™, which provides an additional protective collar to further prevent accidental contact with sample fluids on the surface of the stopper. Vacuum collection tubes available in the art are typically deigned to contain volumes of sample fluid ranging from 3 ml to 10 ml and have outside diameters of 10.25 mm to 16 mm and a length of 64 mm to 100 mm. The tubes can include a label, which can be made of a composition known in the art including, but not limited to, paper or plastic. Preferably, the label is a barcode.

In a preferred embodiment, the sampling tube system allows for access to the sample in an automated or semi-automated manner. More preferably, access is via the pipette tip of the present invention, comprising the piercing tip, the chamber of predefined volume, and the filter barrier. Most preferably, the sampling tube system allows closed-tube handling of the sample and operates in a manner that does not require human intervention.

The sampling tube system contains a loading arm that holds and manipulates the sample tube via inflatable membranes holders, wherein the loading arm allows proper positioning of the sample tube closure and the piercing tip of the pipette tip so that aspiration of the sample through the pierced closure occurs. A transfer arm rotates and moves the loading arm to sample multiple tubes in a serial or parallel manner.

The present invention encompasses a pipette sampling system, designed to utilize in a coordinated and automated or semi-automated manner with regard to function and timing, the sample tube, the pipette tip, and the sampling tube system for the sampling of biological samples from closed-tubes. Further, the invention can provide sampling from a plurality of sample tubes and can be integrated with downstream automated and non-automated processing systems for biological macromolecule purification, including but not limited to, the purification of nucleic acid and protein.

BRIEF DESCRIPTION OF THE DRAWINGS

The following detailed description given by way of example, but not intended to limit the invention solely to the specific embodiments described, may best be understood in conjunction with the accompanying drawings in which.

DETAILED DESCRIPTION OF THE INVENTION

Figure 1:
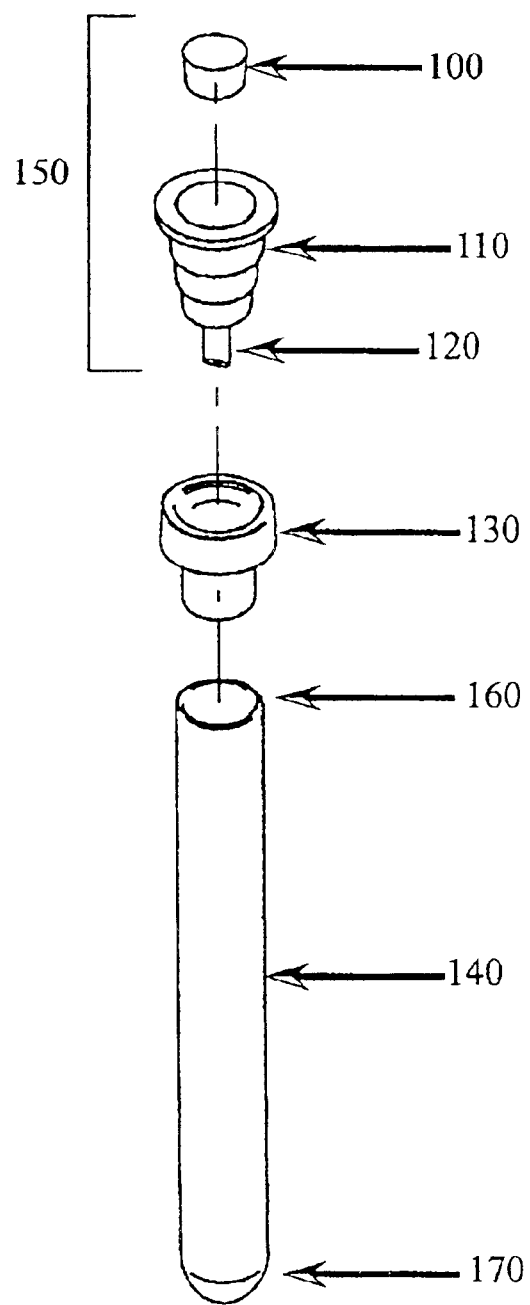
FIG. 1 depicts an embodiment of the pipette tip and a sample tube, preferably but not limited to, a vacuum collection tube, and more preferable, but not limited to, a Vacutainer™ tube.

The following terms used in this disclosure shall have the meaning set forth below:

"Front-end" refers to, for example, the initial process or processes required for a workflow. In the case of the current application, sampling is front-end since it is the initial process that is required before downstream macromolecule purification processes and genomics-based applications can begin, which include, but are not limited to, PCR, sequencing, microarray analysis, SNP detection, and transcriptional profiling.

"Genomics" refers to, for example, characterization and analysis of the genetic composition of organisms at the whole-genome level.

"Genomics technologies" refers to, for example, methods, devices, and components used in the field of genomics.

"Genomics platform" refers to, for example, large numbers of samples processed over a given length of time in an efficient manner.

"Parallel array format" refers to, for example, multiple numbers of sample processed at the same time.

"X-Y-Z robotics" refers to, for example, robotics that control the horizontal, vertical, and diagonal position of an object or group of objects.

The present invention utilizes methods and components for a pipette sampling system that provides closed-tube sampling of biological samples from sample tubes comprising a wide-variety of sample-types. The sample-types include, but are not limited to, biological samples, chemical samples, reagents, fluidic and semi-fluidic samples and the like. Examples of biological samples include, but not limited to, whole blood, plasma, spinal fluid, serum, saliva, sputum, urine, feces, Buccal cells, spermatazoa, solid tissue, bacteria, yeast, viral samples, semen, cultured cell lines, plants and combinations thereof.

The components comprising the current invention include, but are not limited to, a sample tube, a pipette tip, and a sampling tube system. Further, the invention can provide sampling from a plurality of sample tubes, preferably but not limited to 1 to about 200 sample tubes. It is contemplated that the instant invention may be automated, and may be integrated with downstream automated and manual processing systems for biological macromolecule purification, including but not limited to, the purification of nucleic acids and proteins.

In one embodiment, the biological samples are presented to the pipette sampling system in capped containers. Biological samples preferably are of whole-blood, but also may include, but are not limited to, plasma, spinal fluid, serum, saliva, sputum, urine, feces, Buccal cells, spermatozoa, solid tissue, bacteria, yeast, viral samples, semen, cultured cell lines, plants and combinations thereof. Samples, preferably small volume aliquots from about 1 µl to about 5 ml, preferably from about 5 µl to about 1 ml, most preferably from about 20 µl to about 100 µl, are aspirated from closed sample tubes via a pipette tip, comprising a piercing tip, a chamber of defined volume, and a filter barrier. The aspirated sample can then be dispensed and processed by any known method in the art of biological macromolecule purification and can include, but is not limited to, the purification of nucleic acid and protein. A plurality of sample tubes, preferably but not limited to from about 1 to about 200 sample tubes, can be sampled using multiple pipettes and the system can be integrated with automated and non-automated downstream processing systems for biological macromolecule purification, including but not limited to, the purification of nucleic acid and protein.

The pipette sampling system accepts samples presented in closed tubes, preferably but not limited to Vacutainers™. In one embodiment, the sample tubes are accepted in large numbers, preferably but not limited to from about 1 to about 200 sample tubes, and loaded into a sample rack which positions the tubes for sampling. The sample tubes are sealed by a closure at the top of the tube, thereby minimizing or preventing leakage, spillage or aerosol generation. The closure may be any known in the art. The pipette sampling system utilizes piercing tips to remove aliquots of sample from the sample tubes, in which the piercing tips are preferably a component of the pipette tips of the present invention. The automated sample aspiration technique, preferably the sampling tube system of the present invention, allows accurate and precise sampling and prevents carryover and contamination due to leakage, spillage, or aerosol generation of biological sample fluids.

The pipette tip of the present invention allows closed-tube or closed-receptacle sampling, minimizes or prevents cross-contamination, and allows for sampling of small sample volumes. Preferably the small sample volumes can be aliquots from about 1 µl to about 5 ml, preferably from about 5 µl to about 1 ml, or most preferably from about 20 µl to about 100 µl. Closed-tube sampling via the piercing tip, allows for automatic aliquoting of samples from sample tubes, sealed with closures, without destroying or removing the closures of the tubes. The tubes are resealed upon removal of the piercing tip of the pipette tip through the movement of the closure material back into its pre-inserted position.

The pipette tip accommodates sample tubes of varying diameters and lengths. Dimensions of the sample tubes include, for example, 10.25 mm×47 mm, 10.25×64 mm, 13 mm×75 mm, 13 mm×100 mm, 16 mm×100 mm and 16 mm×125 mm.

Preferably, the tubes have an identifier that corresponds to an identifier attached to the samples or to sample paperwork. More preferably, the identifier is a barcode.

In one embodiment of the present invention, a single tube or receptacle is removed from a sample rack. The sample rack may be configured as straight rack, a carousel-type rack or any other configuration known to a skilled artisan. Preferably the tubes are maintained in the sample rack in an upright position. Further, it is also preferable that the racks can hold from about 1 to about 200 tubes.

In a preferred process, a sample tube is removed from the sample rack and presented to the pipette sampling system. Upon insertion of the piercing tip of the pipette tip by the upward motion of a central hub, the sample tube is inverted by about 180°, causing the sample fluid to move to the top of the sample tube. The sample is aspirated, the sample tube is returned to its upright position, and the pipette tip is removed from the tube, the closure is resealed, and the tube is returned to the sample rack. This embodiment utilizes X-Y-Z robotics whereby the exact position of both the tube and the pipette tip can be positioned in space to allow the sampling to occur.

In another embodiment, the sample tubes are loaded onto a carousel rack. As the carousel rotates, a group of sample tubes are aligned with the sampling tube system. Preferably, the group of tubes is greater than or equal to 32 tubes. Multiple tubes are pierced with the pipette tips in a parallel or serial manner, thereby allowing for parallel or serial aspiration of samples.

In yet another embodiment, pipette tips are used in a five-step process. Each of the pipette tips comprises a chamber with a defined volume, a piercing tip, and a hydrophobic sterilizable filter barrier to prevent cross-contamination of sample fluids or aerosols generated from contacting the pipette systems components. In this embodiment, (1) a pipette tip pierces the closed tube, (2) the pierced tube is inverted about 180°, (3) the sample is aspirated, (4) the tube is re-inverted to the starting position, and (5) the pipette tip is withdrawn carrying the aspirated sample.

Referring to FIG. 1, the pipette tip comprises a filter barrier (100), a main chamber of defined volume (110) and a hollow piercing tip (120). In use, the piercing tip (120) pierces the closure (130) which, when properly inserted into a sample tube (140) results in a closed tube that is sufficiently sealed to prevent leakage, spillage, or the release of aerosols. The sample tube (140) comprises a hollow chamber, a top end (160) with an orifice, and a bottom end (170) with a closed surface. The sample tube is preferably, but not limited to, a Vacutainer™.

The filter barrier (100) is preferably one that substantially prevents cross-contamination of fluids or aerosols and/or fluid uptake beyond the chamber, such as into instrument lines. In practice, the filter barrier (100) is hydrophobic and capable of being sterilized by methods known in the art. Suitable filter barriers (100) include, without limitation, Porex™ or any other consumable known in the art. Filter barrier (100) may be cut to size in order to fit into main chamber (110).

In one embodiment, the piercing tip (120) is adapted to pierce a sample tube closure such as those used in Vacutainers™. Suitable materials for piercing tips include, but are not limited to, stainless steel, plastics, polystyrene and polypropylene. Preferably, the piercing tip (120) is disposable. Methods of making the piercing tip include any known in the art.

Most preferably, the pipette tip (150) is adapted to aspiration of small sample volumes. This is particularly suitable for use in aspirating volumes associated with forensic samples. Preferably, the small sample volumes can be from about 1 µl to about 5 ml. More preferably, the small sample volumes are from about 5 µl to about 1 ml. Most preferably, the small sample volumes are from about 20 µl to about 100 µl.

Figure 2:
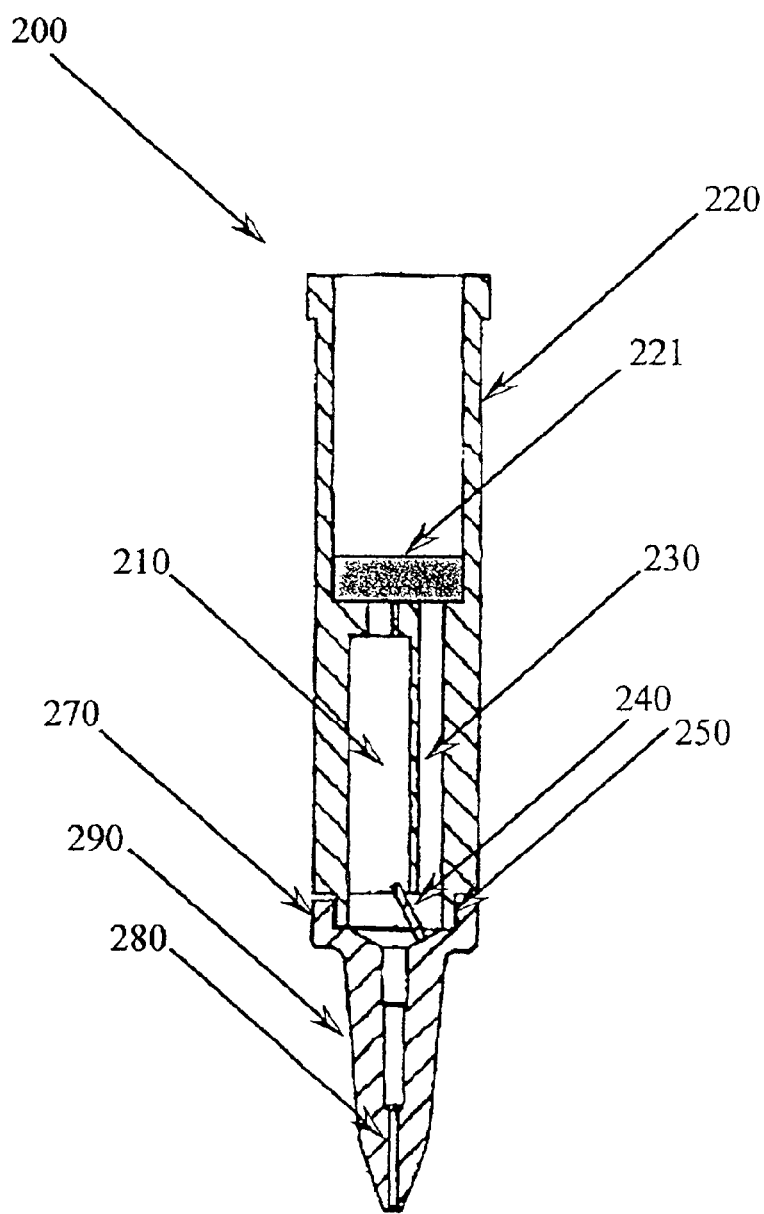
FIG. 2 depicts a detailed embodiment of a pipette tip comprising various components, including the piercing tip.

FIG. 2 refers to a more detailed embodiment of the pipette tip (200). The pipette tip (200) comprises body (220), filter barrier (221), which substantially prevents or blocks fluids and aerosols from escaping the side vent (230), and a body weld (250) and tip weld (270). Piercing tip (290) has an opening (280), through which the sample enters the pipette tip main chamber (210). Side vent (230) functions, for example, to substantially prevent or block excess fluid from passing to filter barrier (221). The sample, when located in the main chamber (210), is prevented from moving into the side vent (230) by the deflector (240). Suitable materials for construction of pipette tip (200) include, without limitation, stainless steel, plastics, polypropylene and polystyrene.

Figure 3:
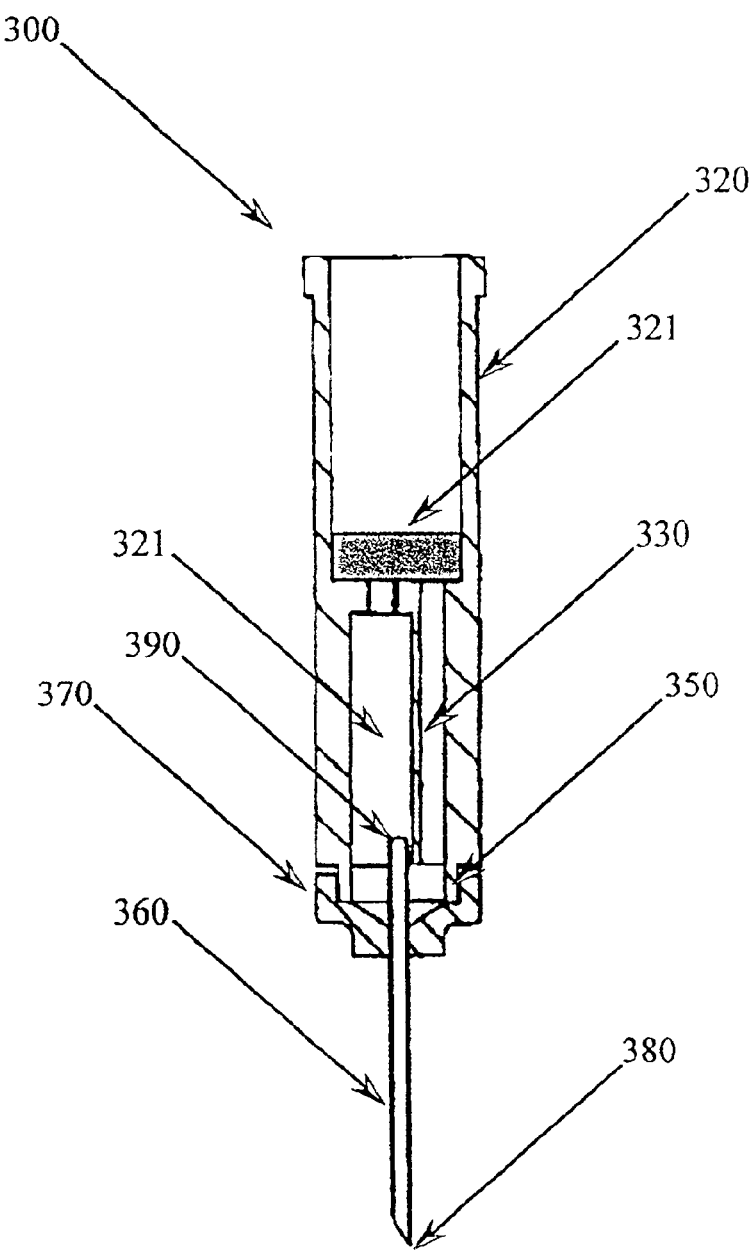
FIG. 3 depicts another detailed embodiment of a pipette tip comprising various components, including the piercing tip in the form of a needle.

FIG. 3 refers to another detailed embodiment of the pipette tip (300). The pipette tip (300) comprises a body (320), a filter barrier (321), which substantially prevents or blocks fluids and aerosols from escaping the side vent (330), and a body weld (350) and tip weld (370). The piercing tip (360), which in this embodiment takes the form of a needle, has an opening (380), in which the sample enters the pipette tip main chamber (321). The sample, when located in the main chamber (321), is prevented from moving into the side vent (330) by the extension of the needle (360) beyond the entrance to the side vent (330). Suitable materials for construction of pipette tip (300) include, without limitation, stainless steel, plastics, polypropylene and polystyrene.

The present invention further comprises a sampling tube system that allows the pipette sampling system to access a sample contained in a tube so as to obtain a defined volume of the sample. Preferably, the tube is a vacuum collection tube or receptacle. More preferably, the tube is a Vacutainer™ tube or a comparable tube or receptacle system available in the current art. Most preferably, the sampling tube system allows access to the sample in an automated or semi-automated manner. Further, access to the biological sample is preferably via the pipette tip of the present invention. Most preferably, the sampling tube system allows closed-tube handling of the sample.

The sampling tube system comprises a loading arm that holds and manipulates the sample tube via an inflatable membrane holder. The loading arm allows proper positioning and alignment of the sample tube closure and the piercing tip of the pipette tip so that aspiration of the sample through the pierced closure occurs. The transfer arm rotates and moves the loading arm to sample multiple tubes serially or in parallel.

In a preferred embodiment, the pipette tip is designed to engage a sampling tube system. In one embodiment, the sampling tube system is operated manually. In another embodiment, the operation of the sampling tube system is automated. In a further embodiment, the pipette tips are packaged loose and unsterilized and are to be sterilized by the end-user. Preferably, the pipette tips are pre-packaged and sterilized. For use in the pipette sampling system, the pipette tips are preferably pre-packaged in a strip holder. Suitable materials for construction of the strip holder include, without limitation, stainless steel, plastics, polypropylene and polystyrene. More preferably, the pipette tips are provided in pre-sterilized strip holders and are ready for use in the pipette sampling system.

Figure 4A:
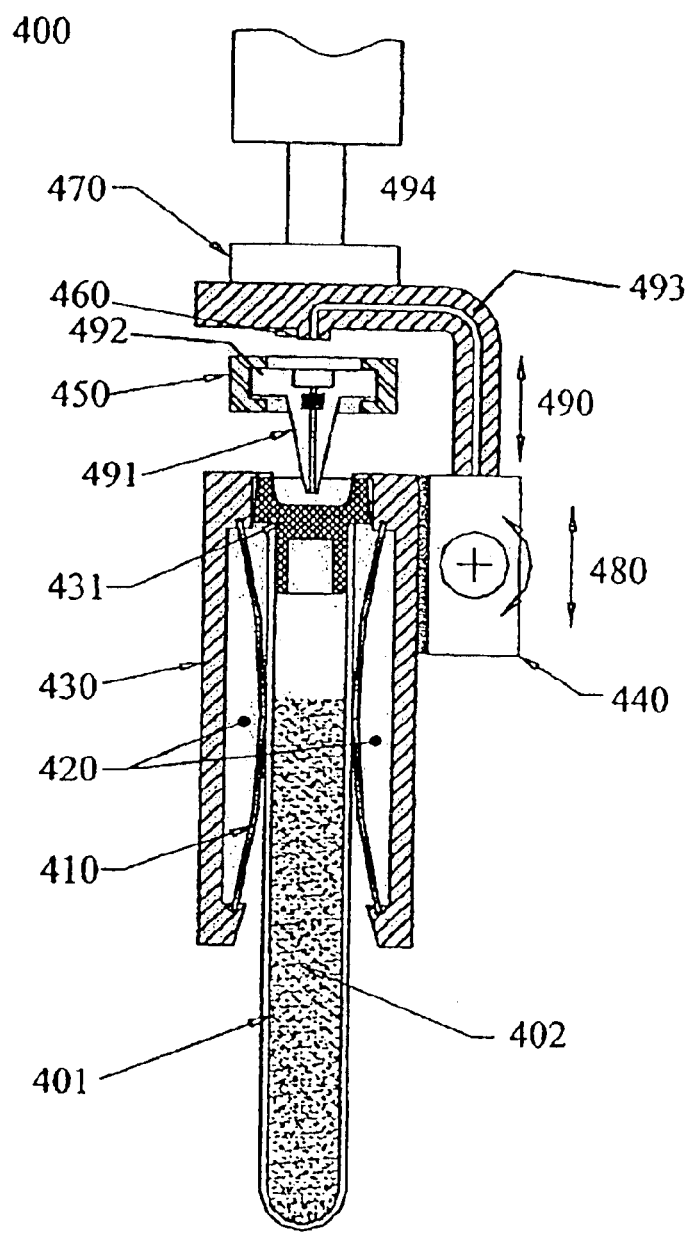
FIG. 4a depicts an embodiment of the sampling tube system wherein the sample tube is loaded onto the system in an upright configuration.

Referring to FIG. 4a, the sampling tube system (400) comprises a sample tube (401) comprising sample (402). Sample tube (401) is positioned upright in loading arm (430). Inflated membrane holders (420) hold sample tube (401) in place. When deflated, membrane holders (420) release sample tube (401). The loading arm is rotated using the transfer arm (440) and positioning element (480) so that the closure (431) can reversibly engage the piercing tip (491) of the pipette tip (492) loaded into a strip holder (450). The pipette tip (492) reversibly engages the transfer arm (440) at the pipettor (460) and puncture cylinder (470) which allows the end of the aspiration tube (493) to functionally connect with the pipette tip (492). The puncture cylinder (470) is held in place by the central hub adapter (494).

Figure 4B:
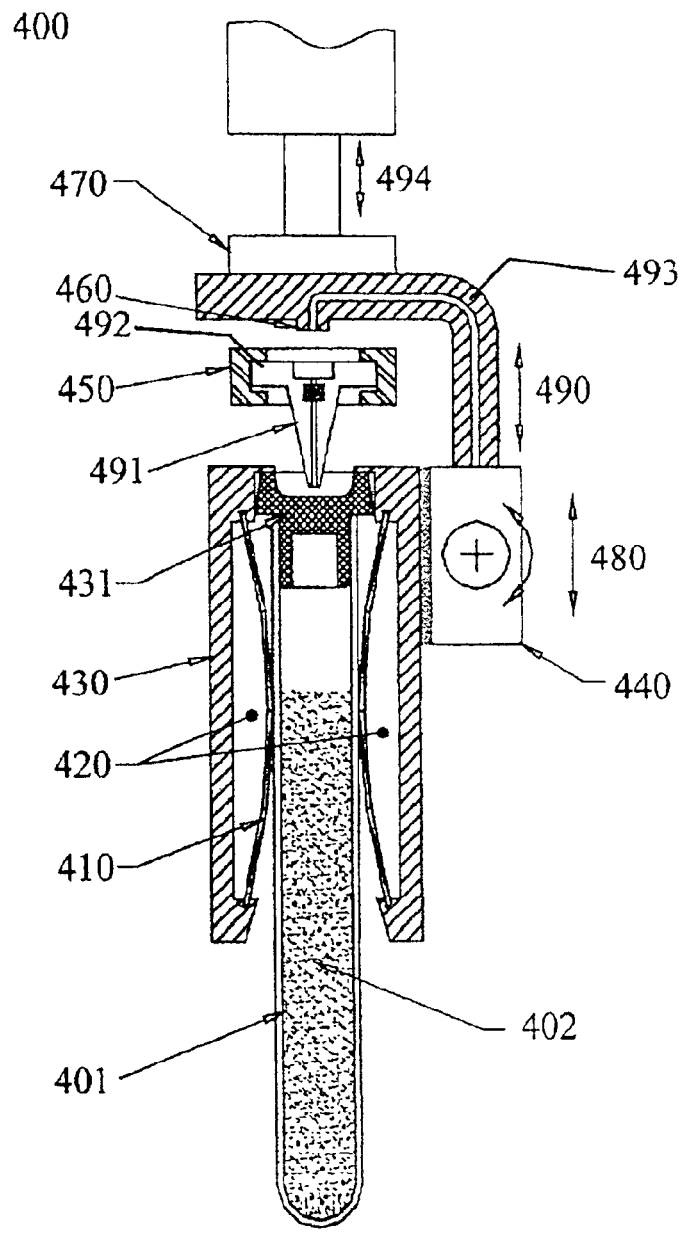
FIG. 4b depicts an embodiment of the sampling tube system wherein the sample tube in an upright position is pierced by the piercing tip.

Referring to FIG. 4b, the sampling tube system (400) comprises a sample tube (401) comprising sample (402). Sample tube (401) is positioned upright in loading arm (430). Inflated membrane holders (420) hold sample tube (401) in place. When deflated, membrane holders (420) release sample tube (401). The loading arm is rotated using the transfer arm (440) and positioning element (480) so that the closure (431) can reversibly engage the piercing tip (491) of the pipette tip (492) loaded into a strip holder (450). The pipette tip (492) reversibly engages the transfer arm (440) at the pipettor (460) and puncture cylinder (470) which allows the end of the aspiration tube (493) to functionally connect with the pipette tip (492). The puncture cylinder (470) is held in place by the central hub adapter (494). Central hub adapter (494) moves upward to allow piercing tip (491) to pierce sample tube (401).

Figure 4C:
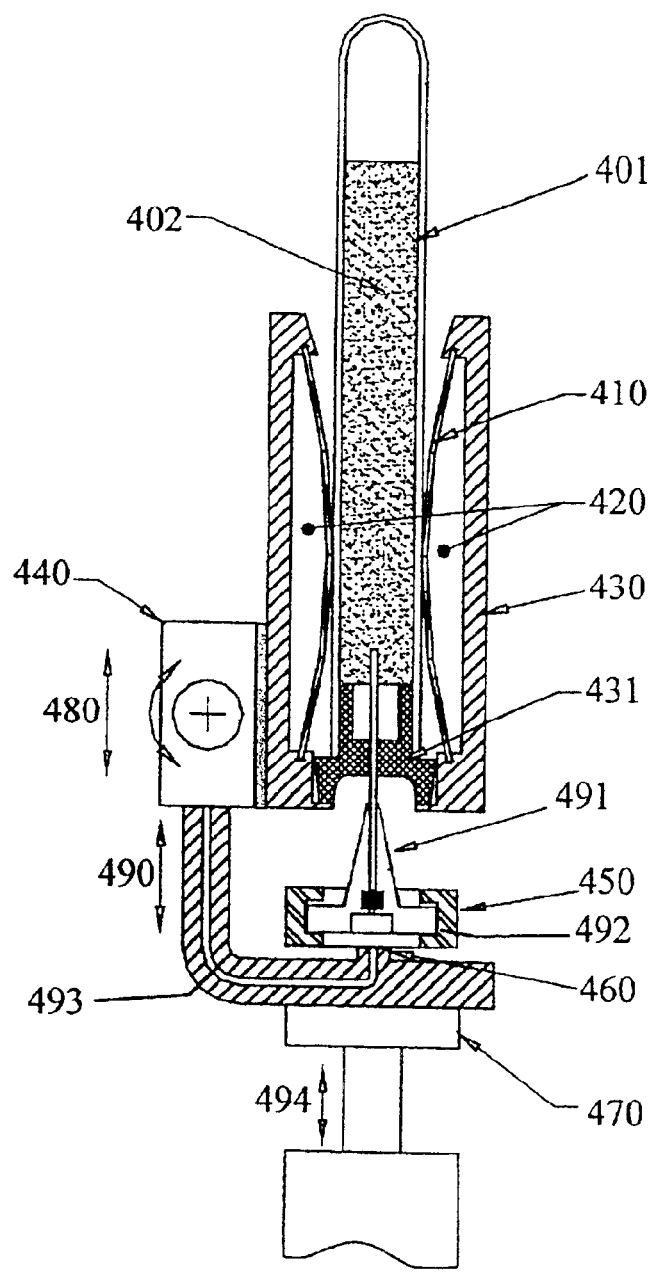
FIG. 4c depicts an embodiment of the sampling tube system wherein the sample tube is inverted for aspiration.

Referring to FIG. 4c, the sampling tube system (400) comprises a sample tube (401) comprising sample (402). Inflated membrane holders (420) hold sample tube (401) in place. When deflated, membrane holders (420) release sample tube (401). The loading arm is rotated using the transfer arm (440) and positioning element (480) so that the closure (431) can reversibly engage the piercing tip (491) of the pipette tip (492) loaded into a strip holder (450). Positioning element (480) rotates sample tube (401) and the biological sample (402) is aspirated by aspiration tube (493) into pipette tip (492).

In one embodiment, the transfer arm delivers the pipette tip, containing the aspirated sample, to a processing tube whereby the sample is dispensed. The puncture cylinder (470) then moves to pull the pipettor (460) out from the disposable pipette tips (492). A new set of pipette tips (492) are automatically inserted into the strip holder (450), thereby discarding the used strip of pipette tips and enabling the instrument to sample from another sample tube or set of tubes.

The dispensed samples are then processed by any method known in the art to yield the purified biological macromolecule, including but not limited to nucleic acid and protein. Nucleic acids include, without limitation DNA and RNA. DNA includes, without limitation, both chromosomal and extrachromosomal. RNA includes, without limitation, MRNA, tRNA, hnRNA, and rRNA.

The nucleic acid isolated can be subsequently used in any method known in the art. Such methods include, without limitation, microarray analysis, manual and automated sequencing, SNP analysis; all types of PCR; restriction fragment analysis, including RFLP (restriction fragment length polymorphism) analysis, in vitro transcription, in vitro translation, and cloning.

DETAILED EXAMPLES

The following examples are set forth to illustrate examples of embodiments in accordance with the invention, it is by no way limiting nor do these examples impose a limitation on the present invention.

Example 1

Loading of Sample Tube

A Vacutainer™ specimen tube was filled with blood and capped. The specimen tube was positioned upright within the loading arm and held in place by inflatable membrane holders.

Example 2

Piercing of Sample Tube

The piercing tip of the pipette tip was positioned above the capped end of the specimen tube by the loading arm. The puncture cylinder pushed the pipette tip downward to reversibly engage and pierce the specimen tube.

Example 3
Aspiration of Sample from Sample Tube

The specimen tube and the pipette tip were rotated about 180 degrees, wherein the specimen tube was substantially inverted. An aliquot of blood was aspirated out of the specimen tube and into the hollow chamber of the pipette tip. The puncture cylinder retracted the pipette tip, thereby disengaged the piercing tip from the specimen tube. The specimen tube was inverted into a substantially upright position. The aliquot of blood was processed by any method known in the art to yield purified DNA.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A device for removing an aliquot of a biological sample from a sealed receptacle comprising said biological sample, comprising:
    a) a hollow chamber of predefined volume having inner and outer walls and top and bottom ends;
    b) a hollow piercing tip having sharp and blunt ends, wherein the blunt end is engaged to the bottom end of the hollow chamber;
    c) a filter barrier engaged to the inner walls of the hollow chamber;
    d) a side vent positioned within the hollow chamber and between the filter barrier and piercing tip; and
    e) a deflector plate separating the hollow chamber and the side vent;
wherein the deflector plate substantially prevents or blocks excess sample from entering into the side vent.

2. The device of claim 1, wherein the piercing tip is retractable within said hollow chamber.

3. The device of claim 1, wherein said biological sample is blood, plasma, spinal fluid, serum, saliva, sputum, urine, feces, Buccal cells, spermatozoa, solid tissue, bacteria, yeast, viral samples, semen, cultured cells lines, plants, or combinations thereof.

4. The device of claim 3, wherein said sealed receptacle is a sample tube.

5. The device of claim 3, wherein the pipette tip and/or the piercing tip is disposable.

6. The device of claim 3, wherein the filter barrier is a hydrophobic sterilizable filter barrier.

7. A device for removing an aliquot of a sample from a sealed receptacle comprising said sample, comprising:
    a) a hollow chamber of predefined volume having inner and outer walls and top and bottom ends;
    b) a hollow piercing tip having sharp and blunt ends, wherein the blunt end is engaged to the bottom end of the hollow chamber;
    c) a filter barrier engaged to the inner walls of the hollow chamber;
    d) a side vent positioned within the hollow chamber and between the filter barrier and piercing tip; and
    e) a deflector plate separating the hollow chamber and the side vent;
wherein the deflector plate substantially prevents or blocks excess sample from entering into the side vent.

* * * * *